(12) United States Patent
Laubacher et al.

(10) Patent No.: US 7,332,910 B2
(45) Date of Patent: Feb. 19, 2008

(54) FREQUENCY DETECTION SYSTEM COMPRISING CIRCUITRY FOR ADJUSTING THE RESONANCE FREQUENCY OF A HIGH TEMPERATURE SUPERCONDUCTOR SELF-RESONANT COIL

(75) Inventors: Daniel B. Laubacher, Wilmington, DE (US); Charles Wilker, Wilmington, DE (US); Jeffrey L. Schiano, Wilmington, DE (US)

(73) Assignees: E.I. du Pont de Nemours and Company, Wilmington, DE (US); The Penn State Research Foundation, University City, PA (US)

( * ) Notice: Subject to any disclaimer, the term of this patent is extended or adjusted under 35 U.S.C. 154(b) by 0 days.

(21) Appl. No.: 10/994,753

(22) Filed: Nov. 22, 2004

(65) Prior Publication Data

US 2006/0012371 A1 Jan. 19, 2006

Related U.S. Application Data

(60) Provisional application No. 60/524,461, filed on Nov. 24, 2003.

(51) Int. Cl.
*G01V 3/00* (2006.01)
(52) U.S. Cl. .................... 324/318; 324/322
(58) Field of Classification Search ............ 324/322, 324/318, 319, 307, 309, 300; 600/410, 422
See application file for complete search history.

(56) References Cited

U.S. PATENT DOCUMENTS

| | | | |
|---|---|---|---|
| 3,373,348 A | 3/1968 | Vanier et al. | |
| 3,764,892 A | 10/1973 | Rollwitz | |
| 4,027,768 A | 6/1977 | Riessen | |
| 4,072,768 A | 2/1978 | Fraser et al. | |
| 4,514,691 A | * 4/1985 | De Los Santos et al. ... | 324/301 |
| 5,004,724 A | * 4/1991 | De .......................... | 505/162 |
| 5,036,279 A | 7/1991 | Jonsen | |
| 5,206,592 A | 4/1993 | Buess et al. | |
| 5,233,300 A | 8/1993 | Buess et al. | |
| 5,258,710 A | 11/1993 | Black et al. | |
| 5,262,394 A | 11/1993 | Wu et al. | |
| 5,276,398 A | 1/1994 | Withers et al. | |
| 5,351,007 A | * 9/1994 | Withers et al. ............ | 324/322 |
| 5,418,213 A | 5/1995 | Tanaka et al. | |
| 5,457,385 A | 10/1995 | Sydney et al. | |
| 5,583,437 A | 12/1996 | Smith et al. | |

(Continued)

FOREIGN PATENT DOCUMENTS

EP 0 426 851 5/1991

(Continued)

OTHER PUBLICATIONS

Miller, et al., "Performance of a High-Temperature Superconducting Probe for In Vivo Microscopy at 2.0 T", Magnetic Resonance in Medicine, (1999) pp. 72-79, vol. 41.

(Continued)

*Primary Examiner*—Brij Shrivastav (57) ABSTRACT

The use of a circuit to adjust the resonance frequency of a high temperature superconductor self-resonant transmit, receive, or transmit and receive coil results in improved performance. The circuit is useful in a frequency detection system, especially in a nuclear quadrupole resonance detection system.

34 Claims, 4 Drawing Sheets

U.S. PATENT DOCUMENTS

| | | | |
|---|---|---|---|
| 5,585,723 A * | 12/1996 | Withers | 324/318 |
| 5,592,083 A | 1/1997 | Magnuson et al. | |
| 5,594,338 A | 1/1997 | Magnuson | |
| 5,656,937 A | 8/1997 | Cantor | |
| 5,661,400 A | 8/1997 | Plies et al. | |
| 5,750,473 A | 5/1998 | Shen | |
| 5,751,146 A | 5/1998 | Hrovat | |
| 5,804,967 A | 9/1998 | Miller et al. | |
| 5,814,987 A | 9/1998 | Smith et al. | |
| 5,814,989 A | 9/1998 | Smith et al. | |
| 5,814,992 A * | 9/1998 | Busse-Grawitz et al. | 324/318 |
| 5,872,080 A | 2/1999 | Arendt et al. | |
| 5,952,269 A * | 9/1999 | Ma et al. | 505/325 |
| 5,973,495 A | 10/1999 | Mansfield | |
| 5,986,455 A | 11/1999 | Magnuson | |
| 5,999,000 A | 12/1999 | Srinivasan | |
| 6,025,719 A | 2/2000 | Anderson | |
| 6,054,856 A | 4/2000 | Garroway et al. | |
| 6,088,423 A | 7/2000 | Krug et al. | |
| 6,091,240 A | 7/2000 | Smith et al. | |
| 6,104,190 A | 8/2000 | Buess et al. | |
| 6,108,569 A | 8/2000 | Shen | |
| 6,150,816 A | 11/2000 | Srinivasan | |
| 6,166,541 A | 12/2000 | Smith et al. | |
| 6,169,399 B1 | 1/2001 | Zhang et al. | |
| 6,194,898 B1 * | 2/2001 | Magnuson et al. | 324/300 |
| 6,201,392 B1 | 3/2001 | Anderson et al. | |
| 6,218,943 B1 | 4/2001 | Ellenbogen | |
| 6,242,918 B1 | 6/2001 | Miller et al. | |
| 6,291,994 B1 | 9/2001 | Kim et al. | |
| 6,335,622 B1 * | 1/2002 | James et al. | 324/318 |
| 6,370,404 B1 | 4/2002 | Shen | |
| D459,245 S | 6/2002 | Power | |
| 6,420,872 B1 | 7/2002 | Garroway et al. | |
| 6,486,838 B1 | 11/2002 | Smith et al. | |
| 6,538,445 B2 | 3/2003 | James et al. | |
| 6,541,966 B1 | 4/2003 | Keene | |
| 6,556,013 B2 * | 4/2003 | Withers | 324/322 |
| 6,566,873 B1 | 5/2003 | Smith et al. | |
| 6,590,394 B2 | 7/2003 | Wang et al. | |
| 6,617,591 B1 | 9/2003 | Simonson et al. | |
| 6,653,917 B2 | 11/2003 | Kang et al. | |
| 6,751,489 B2 * | 6/2004 | Shen | 505/210 |
| 6,751,847 B1 * | 6/2004 | Brey et al. | 29/606 |
| 6,777,937 B1 | 8/2004 | Miller et al. | |
| 6,819,109 B2 | 11/2004 | Sowers et al. | |
| 6,822,444 B2 | 11/2004 | Lai | |
| 6,847,208 B1 | 1/2005 | Crowley et al. | |
| 6,952,163 B2 | 10/2005 | Muey et al. | |
| 6,956,476 B2 | 10/2005 | Buess et al. | |
| 6,958,608 B2 * | 10/2005 | Takagi et al. | 324/318 |
| 7,049,814 B2 | 5/2006 | Mann | |
| 7,106,058 B2 | 9/2006 | Wilker et al. | |
| 2002/0068682 A1 | 6/2002 | Shen | |
| 2002/0153891 A1 | 10/2002 | Smith et al. | |
| 2002/0156362 A1 | 10/2002 | Bock et al. | |
| 2002/0169374 A1 | 11/2002 | Jevtic | |
| 2002/0190715 A1 | 12/2002 | Marek | |
| 2003/0020553 A1 | 1/2003 | Gao | |
| 2003/0062896 A1 | 4/2003 | Wong et al. | |
| 2003/0071619 A1 | 4/2003 | Sauer et al. | |
| 2003/0119677 A1 | 6/2003 | Oiyan | |
| 2003/0136920 A1 | 7/2003 | Flores et al. | |
| 2004/0124840 A1 | 7/2004 | Reykowski | |
| 2004/0222790 A1 | 11/2004 | Karmi et al. | |
| 2004/0245988 A1 * | 12/2004 | Laubacher | 324/316 |
| 2004/0251902 A1 * | 12/2004 | Takagi et al. | 324/318 |
| 2005/0046420 A1 * | 3/2005 | Laubacher et al. | 324/300 |
| 2005/0104593 A1 | 5/2005 | Laubacher et al. | |
| 2005/0122109 A1 | 6/2005 | Wilker et al. | 324/318 |
| 2005/0140371 A1 * | 6/2005 | Alvarez | 324/322 |
| 2005/0143263 A1 * | 6/2005 | Face | 505/210 |
| 2005/0148391 A1 | 7/2005 | Flexman et al. | |
| 2005/0206382 A1 * | 9/2005 | Laubacher et al. | 324/318 |
| 2005/0248345 A1 | 11/2005 | Alvarez | |
| 2005/0258831 A1 | 11/2005 | Alvarez | |
| 2005/0264289 A1 | 12/2005 | Alvarez | |
| 2005/0270028 A1 | 12/2005 | Alvarez et al. | |
| 2006/0012371 A1 | 1/2006 | Laubacher et al. | |
| 2006/0038563 A1 | 2/2006 | Cisholm et al. | |
| 2006/0082368 A1 * | 4/2006 | McCambridge | 324/318 |
| 2006/0119360 A1 * | 6/2006 | Yamamoto et al. | 324/318 |

FOREIGN PATENT DOCUMENTS

| | | |
|---|---|---|
| EP | 1 122 550 A1 | 8/2001 |
| EP | 1 168 483 | 1/2002 |
| EP | 1 416 291 | 5/2004 |
| EP | 1 477 823 A | 11/2004 |
| GB | 2 286 248 | 8/1995 |
| GB | 2 289 344 | 11/1995 |
| JP | 05 269108 | 10/1993 |
| JP | 07 265278 | 10/1995 |
| WO | WO92/17793 | 10/1992 |
| WO | WO92/17794 | 10/1992 |
| WO | WO92/19978 | 11/1992 |
| WO | WO92/21989 | 12/1992 |
| WO | WO94/05022 | 3/1994 |
| WO | WO95/34096 | 12/1995 |
| WO | 96/39636 | 12/1996 |
| WO | WO96/39636 | 12/1996 |
| WO | WO96/39638 | 12/1996 |
| WO | WO98/37438 | 8/1998 |
| WO | WO98/54590 | 12/1998 |
| WO | WO99/45409 | 9/1999 |
| WO | WO99/50689 | 10/1999 |
| WO | WO 00/70356 | 11/2000 |
| WO | WO 02/082115 A2 | 10/2002 |
| WO | WO 02/098364 | 12/2002 |
| WO | WO 03/014700 | 2/2003 |
| WO | WO 03/040761 | 5/2003 |
| WO | WO 03/096041 | 11/2003 |
| WO | WO 2004/001454 A | 12/2003 |
| WO | WO 04/102596 | 11/2004 |
| WO | WO 05/059582 A1 | 6/2005 |

OTHER PUBLICATIONS

W.H. Wong, et al., "HTS Coils for High Resolution Nuclear Magnetic Resonance Spectroscopy", Advances in Cryogenic Engineering, (1996), pp. 953-959, New York.

V. Kotsubo et al., "Cryogenic System for a High Temperature Superconductor NMR Probe", Advances in Cryogenic Engineering, Jul. 17, 1995, vol. 41, pp. 1857-1864, New York.

Kushida, et al., "Dependence on the Pure Quadrupole Resonance Frequency on Pressure and Temperature", Physical Review, (Dec. 1956), pp. 1364-1377, vol. 104, No. 5, Massachusetts.

Vanier, "Temperature Dependence of the Pure Nuclear Quadrupole Resonance Frequency in KC103", Canadian Journal of Physics, (Nov. 1960), pp. 1397-1405, vol. 38, No. 11, Canada.

Smith, et al., "Nitrogen Electric Quadrupole and Proton Magnetic Resonances in Thiourea", Journal of Chemical Physics, (Oct. 1964), pp. 2403-2416, vol. 41, No. 8, New York.

Turner, C.W., High temperature superconductor circuit components for cryogenic microwave systems, Electrical and Computer Engineering, 1993, Canadian Conference on Vancouver, BC Canada Sep. 14, 1993 XP 010118071.

W. A. Edelstein et al., A signal-to-noise calibration procedure for NMR imaging systems, Medical Physics, vol. 11 (2) Mar./Apr. 1984, pp. 180-185.

Charles Wilker, "HTS Sensors for NQR Spectroscopy", vol. 1, pp. 143-146, 2004.

Anders Stensgaard, "Optimized Design of the Shielded-Loop Resonator", Journal of Magnetic Resonance, 122, 120-126 (1996), Article No. 0187.

He, D.F. et al., "Metal detector based on high-Tc RF SQUID", Physica C 378-381 (2002) pp. 1404-1407.

Bendall, et. al., "Elimination of Coupling between Cylindrical Transmit Coils and Surface-Receive Coils for in Vivo NMR" Magnetic Resonance in Medicine v3 p. 157-163, 1986.

Colton, et. al., "Making the World a Safer Place", Science, v.299, i.5611, Pgd.1324-1325, Feb. 2006.

Fisher, et al., "A Versatile Computer-Controlled Pulsed Nuclear Quadrupole Resonance Spectrometer", Review of Scientific Instruments, v70, No. 12, p. 4678, Dec. 1999.

Roemer, et. al., "The NMR Phased Array", Magnetic Resonance In Medicine 16, pp. 192-225, 1990.

Landers, et al., "Electronic Effects and Molecular Motion in β-Octahydro-1,3,5,7-tetranitro-1,3,5,7-tetrazocine Bases on $^{14}$N Nuclear Quadrupole Resonance Spectroscopy", American Chemical Society, J. Phys. Chem., 85, pp. 2618-2623, 1981.

Karpowicz, et. Al., "Librational Motion of Hexahydro-1,3,5-trinitro-s-triazine Based on the Temperature Dependence of the Nitrogen-14 Nuclear Quadrupole Resonance Spectra: The Relationship to Condensed-Phase Thermal Decomposition", American Chemical Society, J. Phys. Chem. 87 , pp. 2109-2112, 1983.

Volpicelli, et al., "Locked rf Spectrometer for Nuclear Quadrupole Resonance", The Review of Scientific Instruments, v.25, No. 2, pp. 150-153, Feb. 1965.

Benedek, et. al., "Precise Nuclear Resonance Thermometer", The Review of Scientific Instruments, v.28, No. 2, pp. 92-95, Feb. 1957.

Ernst, "Magnetic Resonance with Stochastic Excitation", Journal of Magnetic Resonance 3, pp. 10-27, 1970.

Klainer, et. al., "Fourier Transform Nuclear Quadrupole Resonance Spectroscopy", Fourier, Hadamard, and Hilbert Transforms in Chemistry, pp. 147-182, 1982.

Withers, R.S. et al., "Thin-Film HTD Probe Coils For Magnetic-Resonance Imaging", IEEE Transactions On Applied Superconductivity, vol. 3, pp. 2450-2453, Mar. 1993.

Hill Howard, D.W. et al., "Improved Sensitivity Of NMR Spectroscopy Probes By Use Of High-Temperature Superconductive Detection Coils", IEEE Transactions On Applied Superconductivity, vol. 7, pp. 3750-3753, Jun. 1997.

Black, R.D. et al., "Performance Of A High-Temperature Superconducting Resonator For High-Field Imaging", Journal Of Magnetic Resonance, pp. 74-80 (1995).

Black, R.D. et al., "A High-Temperature Superconducting Receiver For Nuclear Magnetic Resonance Microscopy", Science, vol. 259, pp. 793-795 Feb. 5, 1993.

Garroway, et al., "Remote Sensing By Nuclear Quadrupole Resonance", IEEE Transactions on Geoscience and Remote Sensing, Jun. 2001, pp. 1108-1118, vol. 39, No. 6.

Garroway, et al., "Narcotics and Explosives Detection by 14N pure NQR", SPIE, 1993, pp. 318-327, vol. 2092, Maryland.

Hirschfeld, et al., "Short Range Remote NQR Measurements", Journal of Molecular Structure, 1980, pp. 63-77, vol. 58, The Netherlands.

* cited by examiner

FREQUENCY DETECTION SYSTEM COMPRISING CIRCUITRY FOR ADJUSTING THE RESONANCE FREQUENCY OF A HIGH TEMPERATURE SUPERCONDUCTOR SELF-RESONANT COIL

This application claims the benefit of U.S. Provisional Application No. 60/524,461, filed Nov. 24, 2003, which is incorporated in its entirety as a part hereof for all purposes.

FIELD OF THE INVENTION

This invention relates to the use of a circuit to adjust the resonance frequency of a high temperature superconductor self-resonant coil, and to a frequency detection system comprised of such a coil and circuit.

BACKGROUND OF THE INVENTION

The use of nuclear quadrupole resonance (NQR) as a means of detecting explosives and other contraband has been recognized for some time—see e.g. T. Hirshfield et al, *J. Molec. Struct.* 58, 63 (1980); A. N. Garroway et al, *Proc. SPIE* 2092, 318 (1993); and A. N. Garroway et al, *IEEE Trans. on Geoscience and Remote Sensing*, 39, pp. 1108-1118 (2001). NQR provides some distinct advantages over other detection methods. NQR requires no external magnet such as required by nuclear magnetic resonance. NQR is sensitive to the compounds of interest, i.e. there is a specificity of the NQR frequencies.

One technique for measuring NQR in a sample is to place the sample within a solenoid coil that surrounds the sample. The coil provides a radio frequency (RF) magnetic field that excites the quadrupole nuclei in the sample and results in their producing their characteristic resonance signals. This is the typical apparatus configuration that might be used for scanning mail, baggage or luggage. There is also need for a NQR detector that permits detection of NQR signals from a source outside the detector, e.g. a wand detector, that could be passed over persons or containers as is done with existing metal detectors. Problems associated with such a detector using conventional systems are the decrease in detectability with distance from the detector coil, and the associated equipment needed to operate the system.

A detection system can have one or more coils that both transmit and receive, or it can have separate coils that only transmit and only receive. A transmit, or transmit and receive, coil of an NQR detection system provides a radio frequency (RF) magnetic field that excites the quadrupole nuclei in the sample, and results in their producing their characteristic resonance signals that the coil detects. The NQR signals have low intensity and short duration.

The transmit, receive, or transmit and receive, coil preferably has a high quality factor (Q). The transmit, receive, or transmit and receive, coil has typically been a copper coil and therefore has a Q of about $10^2$. It is advantageous to use a transmit, receive, or transmit and receive, coil made of a high temperature superconductor (HTS) rather than copper since the HTS self-resonant coil has a Q of the order of $10^3$–$10^6$. The large Q of the HTS self-resonant coil produces large magnetic field strengths during the RF transmit pulse and does so at lower RF power levels. This dramatically reduces the amount of transmitted power required to produce NQR signals for detection, and thereby reduces the size of the RF power supply sufficiently so that it can be run on portable batteries.

The large Q of the HTS self-resonant coil also plays an important role during the receive time. In view of the low intensity NQR signal, it is important to have a signal-to-noise ratio (S/N) as large as possible. As the signal-to-noise (S/N) ratio is proportional to the square root of Q, the use of the HTS self-resonant coil results in an increase in S/N by a factor of 10-100 over that of the copper system. These advantages during both the transmit and the receive times enable a detector configuration that is small and portable. It is important that the transmit, receive, or transmit and receive, coil is tunable so that the resonance frequency of the respective coil can be adjusted after fabrication to the NQR frequency.

An object of the present invention is to provide for the adjustment of the resonance frequency of a high temperature superconductor self-resonant transmit, receive, or transmit and receive, coil to enhance its use in a frequency detection system.

SUMMARY OF THE INVENTION

This invention provides a circuit to adjust the resonance frequency of a high temperature superconductor self-resonant transmit, receive, or transmit and receive, coil, wherein the circuit is comprised of a single loop or coil to inductively couple the circuit to the high temperature superconductor self-resonant transmit, receive, or transmit and receive, coil; a reactance in series with the single loop or coil; and means for connecting the reactance to, and disconnecting the reactance from, the single loop or coil.

Preferably, the reactance is one that can be varied in order to provide flexibility in adjusting the resonance frequency of the high temperature superconductor self-resonant transmit, receive, or transmit and receive, coil. The means for connecting the reactance to, and disconnecting the reactance from, the single loop or coil may include at least one mechanical switch and/or electrical switch such as a diode. Preferably, the high temperature superconductor self-resonant transmit, receive, or transmit and receive, coil is a planar or surface coil. Preferably, the single loop or coil inductively coupling the circuit to the high temperature superconductor self-resonant transmit, receive, or transmit and receive coil, is a high temperature superconductor single loop or coil, and more preferably, is a high temperature superconductor single loop.

This invention also provides a frequency detection system comprising a high temperature superconductor self-resonant transmit, receive, or transmit and receive, coil, and a circuit to adjust the resonance frequency of the high temperature superconductor self-resonant transmit, receive, or transmit and receive, coil; wherein the circuit is comprised of a single loop or coil to inductively couple the circuit to the high temperature superconductor self-resonant transmit, receive, or transmit and receive, coil, a reactance in series with the single loop or coil, and means for connecting the reactance to, and disconnecting the reactance from, the single loop or coil. This frequency detection system, with the circuit to adjust the resonance frequency of the high temperature superconductor self-resonant transmit, receive, or transmit and receive, coil, is especially useful for detecting nuclear quadrupole resonance, and particularly, for detecting the nuclear quadrupole resonance of explosives, drugs and other contraband.

DETAILED DESCRIPTION OF THE PREFERRED EMBODIMENTS

The use of the circuit of this invention enables the adjustment of the resonance frequency of a high temperature superconductor self-resonant transmit, receive, or transmit and receive, coil. This adjustment of the resonance frequency of the self-resonant coil can be very useful since it is difficult to fabricate a coil having the exact resonance frequency desired. In addition, it can be important to be able to adjust the resonance frequency of the self-resonant coil to match a specific frequency, e.g. the frequency, $f_{NQR}$, of the NQR of interest.

When detecting a frequency, it is important that the resonance frequency of the transmit, or transmit and receive, coil during the transmit mode, i.e. the excitation mode, be identical to the resonance frequency of the receive, or transmit and receive, coil during the receive mode, i.e. the detection mode. This is especially important for low intensity and short duration signals such as NQR signals.

The circuit of the invention that provides for the adjustment of the resonance frequency is comprised of (i) a single loop or coil to inductively couple the circuit to the high temperature superconductor self-resonant transmit, receive, or transmit and receive, coil; (ii) a reactance in series with the single loop or coil; and (iii) means for connecting the reactance to, and disconnecting the reactance from, the single loop or coil. The single loop or coil can be made of a regular conductor, such as copper, or a high temperature superconductor. The reactance can be an inductance, capacitance or combination of both. Preferably, the reactance can be varied so that the resonance frequency can be adjusted to more than one frequency. The means for connecting the reactance to, and disconnecting the reactance from, the single loop or coil, whether the reactance includes capacitors or inductors or both, may include at least one mechanical switch and/or electrical switch such as a diode.

One way of accomplishing a variable reactance is to have the reactance comprised of a number of capacitors in parallel, each of which can be individually connected to or disconnected from the single loop or coil. Alternatively, a variable reactance can be comprised of a number of inductors in series, each of which can be individually connected to or disconnected from the single loop or coil by a switch or diode that can short-circuit the inductor and thereby essentially remove it from the circuit.

Figure 1:
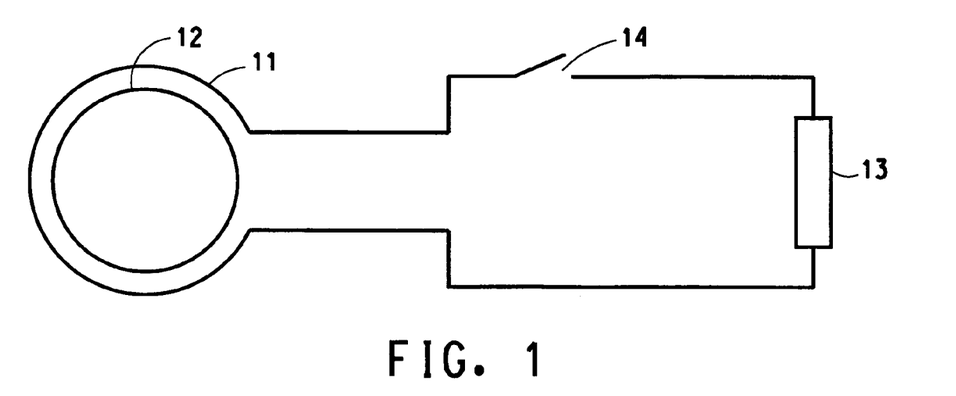
FIG. 1 shows a schematic drawing of the circuit of the invention for adjusting the resonance frequency.

A schematic diagram of the circuit is shown in FIG. 1. The circuit is shown with a single loop 11 that inductively couples the circuit to the high temperature superconductor self-resonant transmit, receive, or transmit and receive, coil 12. Additional loops, i.e. a coil, can be used to provide the desired coupling. Connected to the single loop 11 is a reactance 13 and a switch 14 that connects and disconnects the reactance 13 to the single loop 11. The switch 14 can be a mechanical switch, or it can be an electrical switch such as a diode that conducts above a certain applied voltage.

Figure 2:
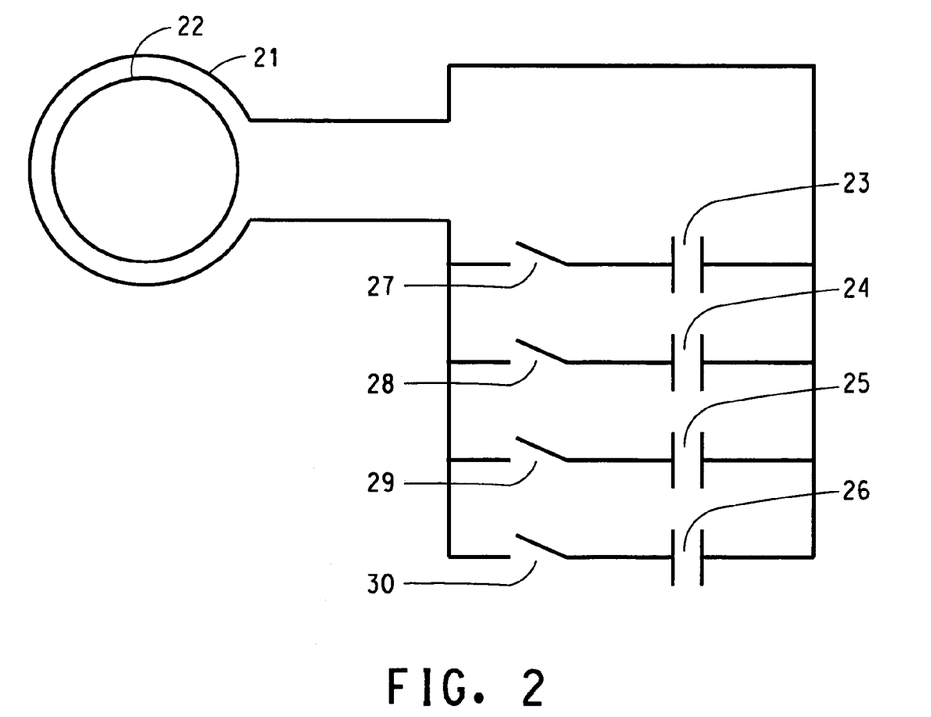
FIG. 2 shows a schematic drawing of one embodiment of the circuit of the invention for adjusting the resonance frequency.

Preferably, the reactance is variable and various portions of the reactance can be connected to and disconnected from the single loop. A schematic diagram of one such embodiment of the circuit of the invention is shown in FIG. 2. The circuit is shown with a single loop 21 that inductively couples the circuit to the high temperature superconductor self-resonant transmit, receive, or transmit and receive, coil 22. In this embodiment, the reactance is variable in the sense that it is comprised of four capacitors 23, 24, 25 and 26 in parallel, and four switches 27, 28, 29, and 30. This permits various combinations of the capacitors to be connected to single loop 21; which can thereby provide various capacitances and, as a result, provide different adjustments to the resonance frequency of the self-resonant coil. More or fewer capacitors can be used in parallel depending upon the desired variation in resonance frequency.

In another embodiment, the reactance is comprised of inductors placed in series with a switch in parallel with each inductor. When the switch is open the inductor is in series with the single loop or coil. When the switch is closed, the switch short-circuits the inductor and essentially removes it from the circuit.

The planar or surface coil preferred for use as the high temperature superconductor self-resonant transmit, receive or transmit and receive, coil has a HTS coil configuration on only one side of the substrate, or has essentially identical HTS coil configurations on both sides of the substrate.

It is often advantageous to be able to fine tune the resonance frequency. One means for accomplishing such tuning is to use two coupled high temperature superconductor self-resonant coils. The resonance frequency of the fundamental symmetric mode of the two coupled high temperature superconductor self-resonant coils can be varied by mechanically displacing one coil with respect to the other, and these coupled coils serve as the HTS transmit, receive or transmit and receive, coil.

Preferably, the single loop in the Q-damping circuit is a single loop of copper or HTS on the same substrate as the HTS transmit, receive, or transmit and receive, coil.

Figure 3:
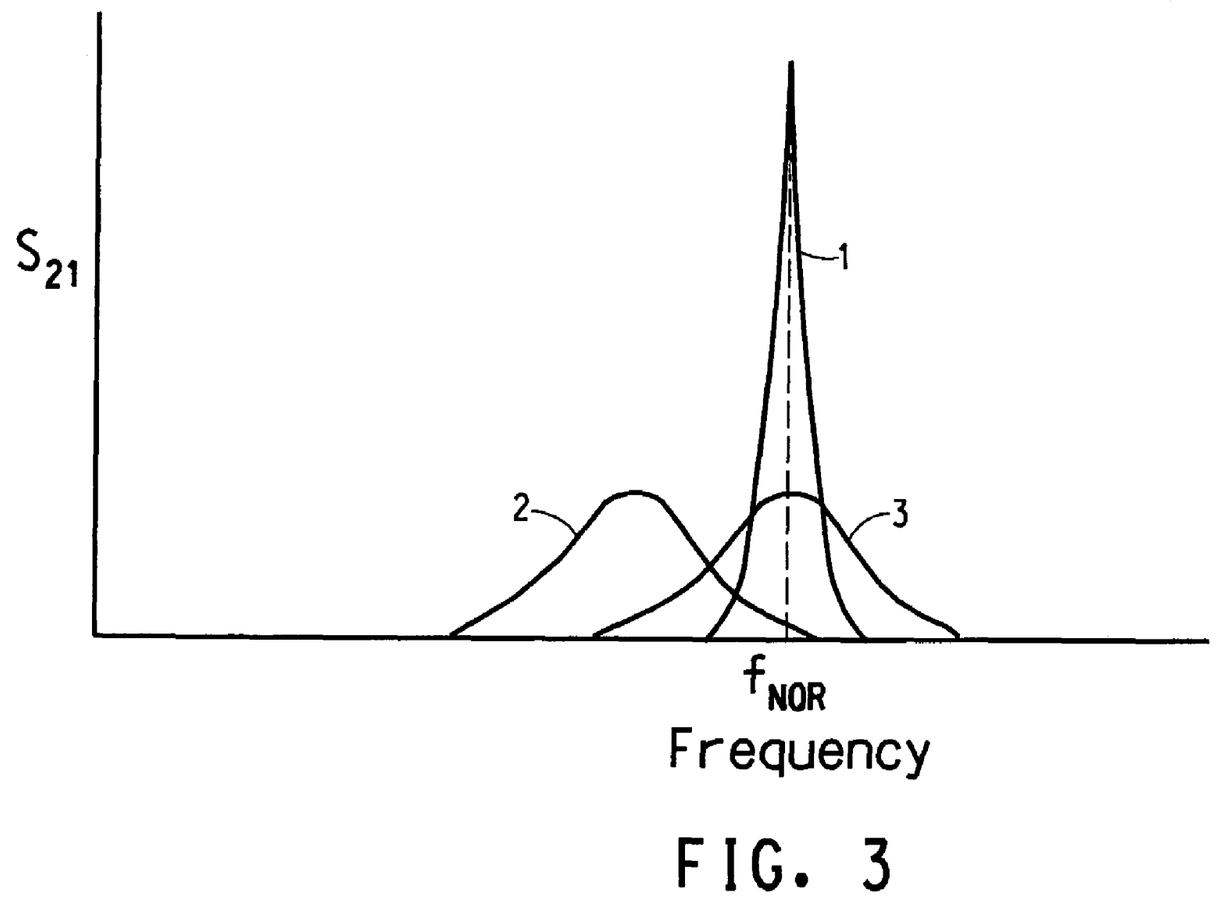
FIG. 3 shows the $S_{21}$ of a HTS self-resonant transmit and receive coil under various conditions.

One difficulty in using a HTS self-resonant transmit, or transmit and receive, coil is that the resonance or center frequency of the coil is power dependent, and shifts to lower frequencies as the power coupled into the coil increases, e.g. as occurs during the transmit period. The $S_{21}$, the magnitude of the transmitting coefficient from the input to the output as a function of frequency, is shown in FIG. 3 for a high temperature superconductor self-resonant transmit, or transmit and receive, coil designed to have a low-transmit-power resonance frequency, $f_{NQR}$, equal to that of the NQR of interest. Curve 1 shows the low-transmit-power-mode, high-Q $S_{21}$ with the resonance frequency $f_{NQR}$. When high power is applied to the coil in the transmit mode, the resonance frequency of the system shifts to a lower frequency, and the Q degrades, as shown by Curve 2. The resonance frequency is no longer $f_{NQR}$, and the fraction of NQR power coupled to the HTS receive, or transmit and receive, coil during the receive mode under these conditions would be small.

The circuit of the instant invention maintains the resonance frequency of the HTS transmit, or transmit and receive, coil at $f_{NQR}$ during the transmit mode. This result is accomplished by an adjustment to the resonance frequency during the high-transmit-power mode, which can be understood by referring to the schematic diagram of simple circuit shown in FIG. 1. The self-resonant coil 12 and the reactance 13, e.g. a capacitance, are chosen so that the low-transmit-power resonance frequency is $f_{NQR}$ when the switch 14 closed, and the reactance 13 is in series with the single loop 11. When high power is applied to the high temperature superconductor self-resonant transmit and receive coil 12 during the transmit mode, the switch is opened to essentially remove the reactance from the circuit, and the resonance frequency remains at $f_{NQR}$. This is indicated by Curve 3 in FIG. 3 where the resonance frequency is $f_{NQR}$, but the Q is still degraded due to the power dependence of the HTS coil. This allows power to be transmitted at the correct frequency during the transmit mode. In the case of a transmit and receive coil, the switch 14 in FIG. 1 is closed for the receive mode so that the resonance frequency is $f_{NQR}$.

The circuit is designed in the following manner to adjust the power dependent resonance frequency. The HTS self-resonant transmit, or transmit and receive, coil and the circuit are designed to provide a resonance frequency equal to the desired $f_{NQR}$. The power dependent resonance frequency shift can be attributed to a kinetic inductance. When the reactance is removed from the circuit by opening the switch, its removal balances the additional kinetic inductance during the high power mode. The power dependent shift in resonance frequency of the HTS self-resonant transmit, or transmit and receive, coil can be observed for the high power expected to be used, and the HTS coil design and the circuit reactance parameters are chosen accordingly.

High temperature superconductors are those that superconduct above 77K. The high temperature superconductors used to form the HTS self-resonant transmit and receive coil are preferably selected from the group consisting of $YBa_2Cu_3O_7$, $Tl_2Ba_2CaCu_2O_8$, $TlBa_2Ca_2Cu_3O_9$, (TlPb)$Sr_2CaCu_2O_7$ and (TlPb) $Sr_2Ca_2Cu_3O_9$. Most preferably, the high temperature superconductor is $YBa_2Cu_3O_7$ or $Tl_2Ba_2CaCu_2O_8$.

The HTS self-resonant transmit, receive, or transmit and receive, coil can be formed by various known techniques. A preferred technique for forming $Tl_2Ba_2CaCu_2O_8$ coils is used in the examples.

Provision must be made for a power supply to supply power for transmitting the RF pulse as well as for related circuitry for processing the detected NQR signal. Provision must also be made for cooling the HTS coil to liquid nitrogen temperature.

The advantageous effects of this invention are demonstrated by a series of examples, as described below. The embodiments of the invention on which the examples are based are illustrative only, and do not limit the scope of the appended claims.

EXAMPLES 1-15

The purpose of these examples is to demonstrate the use of a circuit of the type shown in FIG. 2 to adjust the resonance frequency of a HTS self-resonant coil. The HTS self-resonant coil used is comprised of two coupled essentially identical $Tl_2Ba_2CaCu_2O_8$ planar coils. Each of the coupled coils is on a sapphire ($Al_2O_3$) substrate with the coil design configuration shown in FIG. 4 on both sides of the substrate.

A clean, polished single crystal sapphire substrate with a diameter of 2 inches (5.1 cm) and an approximate thickness of 0.018 inches (0.46 mm) was obtained from Union Carbide Corp. An epitaxial $CeO_2$ buffer layer is grown on both sides of the substrate by off-axis sputter deposition with the substrate temperature held in the range of about 700-800° C. Off-axis magnetron sputtering of a Ba:Ca:Cu oxide target is used to deposit, at room temperature (about 20° C.), an amorphous precursor Ba:Ca:Cu oxide film on the $CeO_2$ buffer layer on both sides of the substrate. This amorphous Ba:Ca:Cu oxide film is about 550 nm thick and had a stoichiometry of about 2:1:2. The precursor film is then thallinated by annealing it in air for about 45 minutes at 850° C. in the presence of a powder mixture of $Tl_2Ba_2Ca_2Cu_3O_{10}$ and $Tl_2O_3$. When this powder mixture is heated, $Tl_2O$ evolves from the powder mixture, diffuses to the precursor film and reacts with it to form the $Tl_2Ba_2CaCu_2O_8$ phase.

Figure 4:
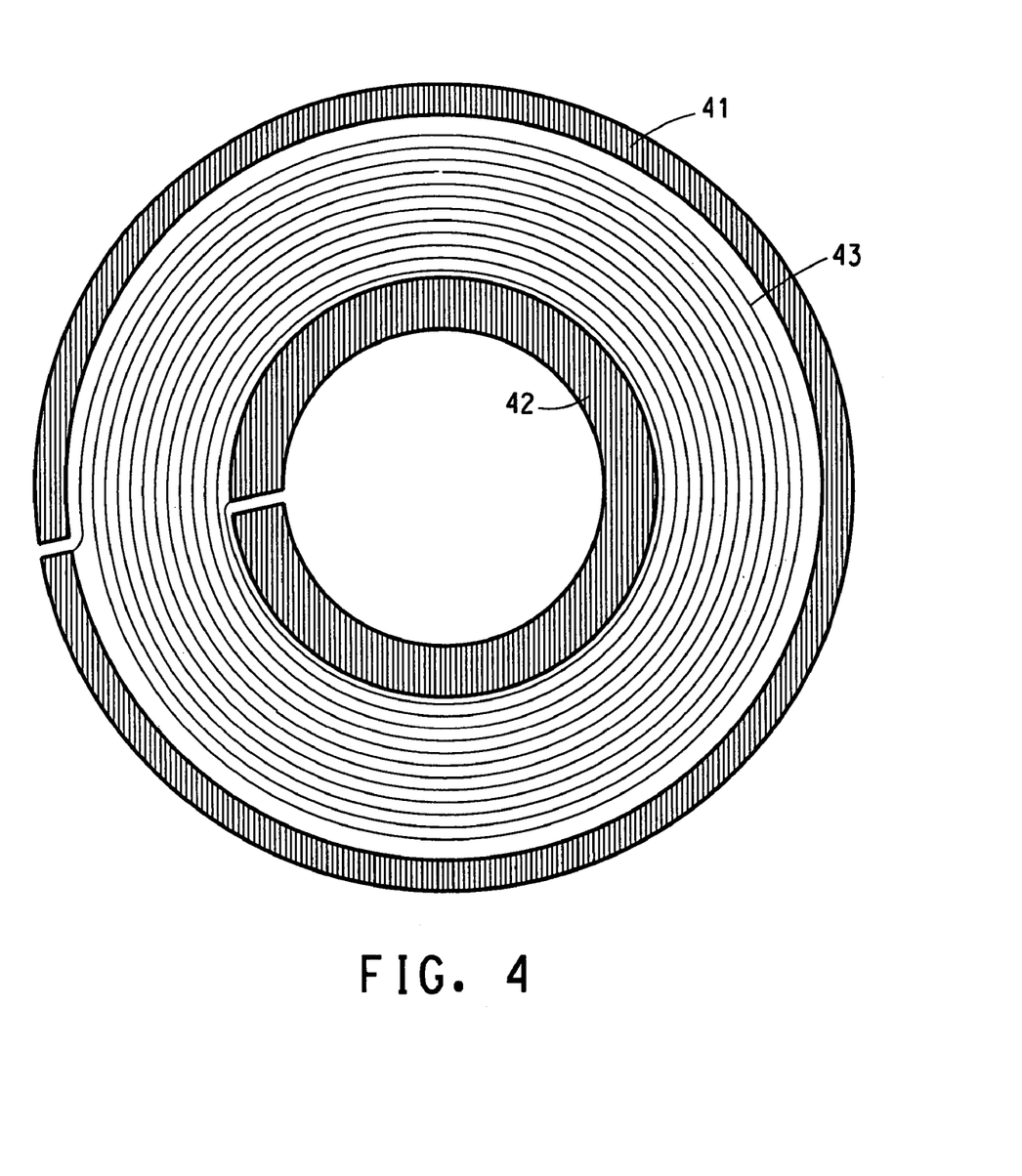
FIG. 4 shows the HTS coil design of the HTS transmit and receive coil used in Examples 1-30.

The sample is then coated with photoresist on both sides and baked. A coil design mask with the design shown in FIG. 4 is prepared. The coil has an inner radius of about 10.5 mm and an outer radius of about 22.5 mm. The outermost HTS ring 41 of the coil is about 2 mm wide and the innermost HTS ring 42 is about 3.5 mm wide. The intermediate HTS rings 43 are about 250 µm wide with about 250 µm gaps between the rings. The coil design mask is then centered on the photoresist covering the $Tl_2Ba_2CaCu_2O_8$ film on the front side of the substrate and exposed to ultraviolet light. The coil design mask is then centered on the photoresist covering the $Tl_2Ba_2CaCu_2O_8$ film on the back side of the substrate and exposed to ultraviolet light. The resist is then developed on both sides of the substrate, and the portion of the $Tl_2Ba_2CaCu_2O_8$ film exposed when the resist is developed is etched away by argon beam etching. The remaining photoresist layer is then removed by an oxygen plasma.

The result is a coil structure comprised of the single crystal sapphire substrate with a $CeO_2$ buffer layer and a high temperature superconductor $Tl_2Ba_2CaCu_2O_8$ pattern of the configuration shown in FIG. 4 centered on the $CeO_2$ buffer layer on each side of the single crystal sapphire substrate. The process is repeated in essentially the same way to produce a second coil essentially identical to the first.

Figure 5A:
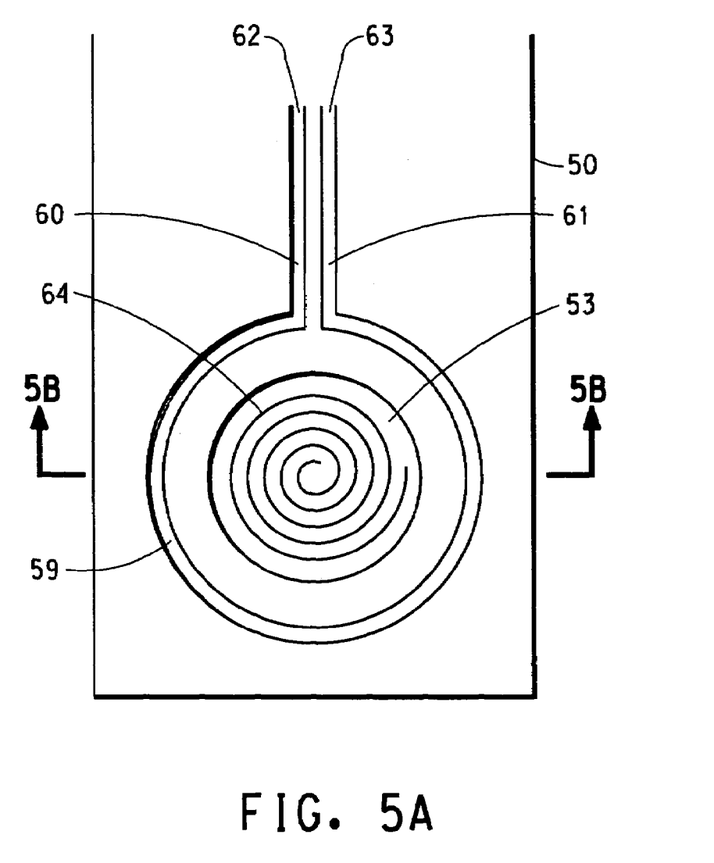
FIGS. 5A and 5B show the holder that was used in Examples 1-30 to hold the HTS coil that is comprised of two coupled HTS self-resonant planar coils and the single loop that inductively couples the circuit of the invention to the HTS coil.
Figure 5B:
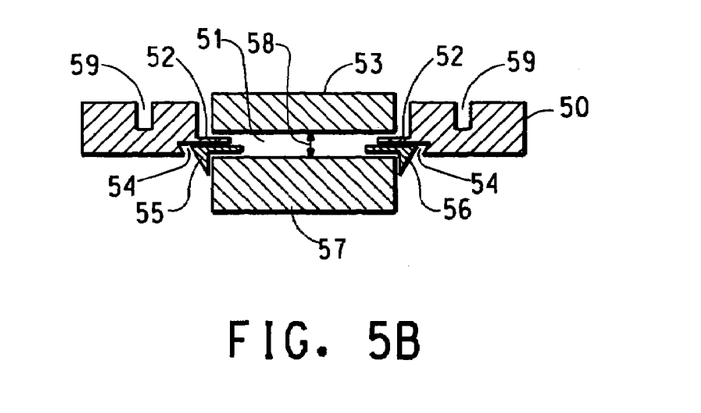

FIG. 5A is a schematic drawing of the top view of holder 50 that holds the two sapphire substrates and the copper single loop. FIG. 5B is a cross section of the holder 50 taken at points "5B"-"5B" of FIG. 5A. The holder 50 is a fiberglass epoxy laminate. A circular hole 51 of radius about ⅞ inch (2.2 cut) is cut near one end of the sample holder 50 A second hole with an outer radius of about 1 inch (2.5 cm) is cut leaving a ledge 52 to hold the one sapphire substrate 53 as shown. On the opposite side of the ledge 52, a cut-out 54 is made to accommodate moveable substrate holders 55 and 56 that serve to hold the other sapphire substrate 57. The two moveable substrate holders 55 and 56 also serve to translate sapphire substrate 57 laterally, i.e. horizontally, with respect to sapphire substrate 53, and thereby enable the resonance frequency of the two coupled HTS coils to be fine tuned. The distance 58 between the two sapphire substrates is 1 mm. A circular groove 59 of radius about 1.1 inch (2.8 cm) surrounding and concentric with the sapphire substrate 53 is cut into the surface of the sample holder 50 along with parallel grooves 60 and 61. A piece of 18 American Wire Gauge copper wire, not shown, is placed in groove 60 beginning at point 62 and extending along groove 60 to the circular groove 59, around circular groove 59 to parallel groove 61, and along groove 61 to point 63. The copper wire in the circular groove 59 Serves as a single loop to inductively couple the FITS transmit and receive coil to the Q-damping circuit. Connections to the four capacitors of the circuit shown in FIG. 2 are made at points 62 and 63. The HTS pattern 64 on one side of the sapphire substrate 53 is indicated in FIG. 5A.

The capacitors 23, 24, 25 and 26 of the circuit shown in FIG. 2 had capacitances of 20, 58, 100 and 220 pF, respectively.

The HTS self-resonant coil is immersed in liquid nitrogen held in a Nalgene® dewar. A pick-up coil comprised of a loop of copper wire is placed about 1 inch (2.5 cm) away from the HTS self-resonant coil with the plane of the pick-up coil parallel to the plane of the coil. The pick-up coil is formed by removing the outer jacket and dielectric spacer from a piece of 0.080 inch (2 mm) coax cable. The loop is formed by bending the inner conductor into a circle and soldering it to the outer jacket of the coax cable just outside the point where the jacket and dielectric are removed. The pick-up coil is connected to an Agilent 8753 Vector Network Analyzer (Agilent Technologies, Palo Alto, Calif.).

The frequency is swept, and the resonance frequency and Q of the HTS coil is measured for each combination of capacitors connected to the single loop. Substrate 57 has been positioned with respect to substrate 53 so that the HTS coil comprised of the two coupled $Tl_2Ba_2CaCu_2O_8$ planar coils has a resonance frequency of 3761.6 kHz and a Q of 2950. This measurement is made with all switches 27, 28, 29 and 30 shown in FIG. 2 open so that there are no capacitors in the circuit of the single loop 21, i.e. the circuit is open and has no effect.

The specification of which switches are closed, using the notation of FIG. 2, and the resulting capacitances in the circuit, are listed in Table I for each example along with the resonance frequencies and Q's of the HTS coil. For instance, for Example 1, switch 27 of FIG. 2 is closed, and switches 28, 29 and 30 are open, so that the capacitance in series with the single loop is 20 pF. For Example 15, all switches are closed, and the capacitance in series with the single loop is 398 pF.

TABLE I

| Example Number | Switches Closed | Capacitance (pF) | Resonance Freq. (kHz) | Q |
| --- | --- | --- | --- | --- |
| Open Circuit | None | 0 | 3761.6 | 2950 |
| 1 | 27 | 20 | 3761.5 | 2840 |
| 2 | 28 | 58 | 3760.5 | 2890 |
| 3 | 27, 28 | 78 | 3760.4 | 2800 |
| 4 | 29 | 100 | 3759.8 | 2710 |
| 5 | 27, 29 | 120 | 3759.5 | 2780 |
| 6 | 28, 29 | 158 | 3758.6 | 2710 |
| 7 | 27, 28, 29 | 178 | 3758.3 | 2690 |
| 8 | 30 | 220 | 3757.1 | 2850 |
| 9 | 27, 30 | 240 | 3756.9 | 2730 |
| 10 | 28, 30 | 278 | 3755.7 | 2540 |
| 11 | 27, 28, 30 | 298 | 3755.4 | 2650 |
| 12 | 29, 30 | 320 | 3754.5 | 2450 |
| 13 | 27, 29, 30 | 340 | 3754.2 | 2440 |
| 14 | 28, 29, 30 | 378 | 3752.9 | 2440 |
| 15 | 27, 28, 29, 30 | 398 | 3752.7 | 2400 |

These results show that the resonance frequency of the HTS coil can be adjusted in small increments by varying the reactance in the circuit inductively coupled to the HTS coil, and that this variation can be accomplished with no significant change in Q. With the set of capacitors used in these examples, the resonance frequency could be varied over a range of 8.9 kHz.

EXAMPLES 16-30

The purpose of these examples is to further demonstrate the use of a circuit of the type shown in FIG. 2 to adjust the resonance frequency of a HTS self-resonant coil. The HTS coil used in these examples is the same HTS self-resonant coil comprised of two coupled essentially identical $Tl_2Ba_2CaCu_2O_8$ planar coils used in Examples 1-15. The same holder, and the same copper single loop coupling the HTS coil to the circuit for adjusting the resonance frequency of the HTS coil as used in Examples 1-15, are used in Examples 16-30. The circuit is identical to that used in Examples 1-15 except that the capacitors 23, 24, 25 and 26 of the circuit shown in FIG. 2 had capacitances of 58, 100, 220 and 300 pF, respectively.

The resonance frequency and Q of the HTS coil is measured for each combination of capacitors connected to the single loop in the same manner as carried out for Examples 1-15. Substrate 57 has been positioned with respect to substrate 53 so that the HTS coil comprised of the two coupled $Tl_2Ba_2CaCu_2O_8$ planar coils has a resonance frequency of 3766.8 kHz and a Q of 2950. This measurement is made with all switches 27, 28, 29 and 30 shown in FIG. 2 open so that there are no capacitors in the circuit of the single loop 21, i.e. the circuit is open and has no effect. The specification of which switches are closed, using the notation of FIG. 2, and the resulting capacitances in the circuit, are listed in Table II for each example along with the resonance frequencies and Q's of the HTS coil.

TABLE II

| Example Number | Switches Closed | Capacitance (pF) | Resonance Freq. (kHz) | Q |
| --- | --- | --- | --- | --- |
| Open Circuit | None | 0 | 3766.8 | 2950 |
| 16 | 27 | 58 | 3765.8 | 2840 |
| 17 | 28 | 100 | 3765.4 | 2890 |
| 18 | 27, 28 | 158 | 3764.3 | 2800 |
| 19 | 29 | 220 | 3762.8 | 2710 |
| 20 | 27, 29 | 278 | 3761.4 | 2780 |
| 21 | 30 | 300 | 3760.8 | 2850 |
| 22 | 28, 29 | 320 | 3760.3 | 2710 |
| 23 | 27, 30 | 358 | 3759.3 | 2730 |
| 24 | 27, 28, 29 | 378 | 3758.8 | 2690 |
| 25 | 28, 30 | 400 | 3758.2 | 2540 |
| 26 | 27, 28, 30 | 458 | 3756.6 | 2650 |
| 27 | 29, 30 | 520 | 3754.7 | 2450 |
| 28 | 27, 29, 30 | 578 | 3752.8 | 2440 |
| 29 | 28, 29, 30 | 620 | 3751.4 | 2440 |
| 30 | 27, 28, 29, 30 | 678 | 3749.3 | 2400 |

These results show that the resonance frequency of the HTS coil can be adjusted in small increments by varying the reactance in the circuit inductively coupled to the HTS coil, and that this variation can be accomplished with no significant change in Q. With the set of capacitors used in these examples, the resonance frequency could be varied over a range of 17.5 kHz.

Where an apparatus of this invention is stated or described as comprising, including, containing, having, being composed of or being constituted by certain components, it is to be understood, unless the statement or description explicitly provides to the contrary, that one or more components other than those explicitly stated or described may be present in the apparatus. In an alternative embodiment, however, the apparatus of this invention may be stated or described as consisting essentially of certain components, in which embodiment components that would materially alter the principle of operation or the distinguishing characteristics of the apparatus would not be present therein. In a further alternative embodiment, the apparatus of this invention may be stated or described as consisting of certain components, in which embodiment components other than those as stated would not be present therein.

Where the indefinite article "a" or "an" is used with respect to a statement or description of the presence of a component in an apparatus of this invention, it is to be understood, unless the statement or description explicitly provides to the contrary, that the use of such indefinite article does not limit the presence of the component in the apparatus to one in number.

What is claimed is:

1. A circuit to adjust the power dependent resonance frequency of a high temperature superconductor self-resonant transmit or transmit and receive coil, wherein the circuit is comprised of
a single loop or coil to inductively couple the circuit to the high temperature superconductor self-resonant coil,
a reactance in series with the single loop or coil, and
means operative while the coil is transmitting for connecting the reactance to, and disconnecting the reactance from, the single loop or coil, the connection and disconnection of the reactance serving to adjust the power dependent resonance frequency of the coil.

2. The circuit of claim 1 wherein the circuit is comprised of a single loop, and the high temperature superconductor self-resonant transmit or transmit and receive coil is a planar coil.

3. The circuit of claim 1 wherein the circuit is comprised of a single loop, and the high temperature superconductor self-resonant transmit or transmit and receive coil is comprised of two coupled high temperature superconductor planar coils.

4. The circuit of any of claims 1-3 wherein the reactance can be varied.

5. A circuit to adjust the resonance frequency of a high temperature superconductor self-resonant coil, comprising:
a single loop or coil to inductively couple the circuit to the high temperature superconductor self-resonant coil;
a variable reactance in series with the single loop or coil, wherein the reactance comprises two or more capacitors in parallel; and
means for connecting the reactance to, and disconnecting the reactance from, the single loop or coil, the means for connecting the reactance to, and disconnecting the reactance from, the single loop or coil enables each of the capacitors to be individually connected to, and disconnected from, the single loop or coil.

6. The circuit of claim 5 wherein the means for connecting the reactance to, and disconnecting the reactance from, the single loop or coil comprises one mechanical or electrical switch for each of the capacitors.

7. A circuit to adjust the resonance frequency of a high temperature superconductor self-resonant coil, comprising:
a single loop or coil to inductively couple the circuit to the high temperature superconductor self-resonant coil;
a variable reactance in series with the single loop or coil, wherein the reactance comprises two or more inductors in series; and
means for connecting the reactance to, and disconnecting the reactance from, the single loop or coil, the means for connecting the reactance to, and disconnecting the reactance from, the single loop or coil enables each of the inductors to be individually connected to, and disconnected from, the single loop or coil.

8. The circuit of claim 7 wherein the means for connecting the reactance to, and disconnecting the reactance from, the single loop or coil comprises one mechanical or electrical switch for each of the inductors.

9. A frequency detection system, comprising:
a high temperature superconductor self-resonant transmit and receive coil; and
a circuit to adjust the power dependent resonance frequency of the high temperature superconductor self-resonant transmit and receive coil;
wherein the circuit is comprised of a single loop or coil to inductively couple the circuit to the high temperature superconductor self-resonant transmit and receive coil,
a variable reactance in series with the single loop or coil, and
means operative while the coil is transmitting for connecting the reactance to, and disconnecting the reactance from, the single loop or coil, the connection and disconnection of the reactance serving to adjust the power dependent resonance frequency of the coil.

10. The frequency detection system of claim 9 wherein the circuit is comprised of a single loop, and the high temperature superconductor self-resonant transmit and receive coil is a planar coil.

11. The frequency detection system of claim 9 wherein the circuit is comprised of a single loop, and the high temperature superconductor self-resonant transmit and receive coil is comprised of two coupled high temperature superconductor planar coils.

12. The frequency detection system of any of claims 9-11 wherein the reactance can be varied.

13. The frequency detection system of any of claims 9-11 which comprises a nuclear quadrupole resonance detection system.

14. The frequency detection system of claim 13 wherein the nuclear quadrupole resonance detection system detects explosives, drugs or other contraband.

15. A frequency detection system comprising:
a high temperature superconductor self-resonant transmit and receive coil;
a circuit to adjust the resonance frequency of the high temperature superconductor self-resonant transmit and receive coil, wherein the circuit comprises a single loop or coil to inductively couple the circuit to the high temperature superconductor self-resonant transmit and receive coil;
a variable reactance in series with the single loop or coil, wherein the reactance is comprised of two or more capacitors in parallel, and
means for connecting the reactance to, and disconnecting the reactance from, the single loop or coil, the means enabling each of the capacitors to be individually connected to, and disconnected from, the single loop or coil.

16. The frequency detection system of claim 15 wherein the means for connecting the reactance to, and disconnecting the reactance from, the single loop or coil comprises one mechanical or electrical switch for each of the capacitors.

17. A frequency detection system comprising:
a high temperature superconductor self-resonant transmit and receive coil;
a circuit to adjust the resonance frequency of the high temperature superconductor self-resonant transmit and receive coil, wherein the circuit comprises a single loop or coil to inductively couple the circuit to the high temperature superconductor self-resonant transmit and receive coil;

a variable reactance in series with the single loop or coil, wherein the reactance is comprised of two or more inductors in series, and means for connecting the reactance to, and disconnecting the reactance from, the single loop or coil, the means enabling each of the inductors to be individually connected to, and disconnected from, the single loop or coil.

18. The frequency detection system of claim 17 wherein the means for connecting the reactance to, and disconnecting the reactance from, the single loop or coil comprises one mechanical or electrical switch for each of the inductors.

19. A frequency detection system, comprising:

a high temperature superconductor self-resonant transmit coil; and a circuit to adjust the power dependent resonance frequency of the high temperature superconductor self-resonant transmit coil;

wherein the circuit is comprised of a single loop or coil to inductively couple the circuit to the high temperature superconductor self-resonant transmit coil, a reactance in series with the single loop or coil, and means operative while the coil is transmitting for connecting the reactance to, and disconnecting the reactance from, the single loop or coil, the connection and disconnection of the reactance serving to adjust the power dependent resonance frequency of the coil.

20. The frequency detection system of claim 19 wherein the single loop or coil is a single loop, and the high temperature superconductor self-resonant transmit coil is a planar coil.

21. The frequency detection system of claim 19 wherein the single loop or coil is a single loop, and the high temperature superconductor self-resonant transmit coil is comprised of two coupled high temperature superconductor planar coils.

22. The frequency detection system of any of claims 19-21 wherein the reactance can be varied.

23. The frequency detection system of any of claims 19-21 which comprises a nuclear quadrupole resonance detection system.

24. The frequency detection system of claim 23 wherein the nuclear quadrupole resonance detection system detects explosives, drugs or other contraband.

25. A frequency detection system comprising:

a high temperature superconductor self-resonant transmit coil;

a circuit to adjust the resonance frequency of the high temperature superconductor self-resonant transmit coil, wherein the circuit comprises a single loop or coil to inductively couple the circuit to the high temperature superconductor self-resonant transmit coil;

a variable reactance in series with the single loop or coil, wherein the reactance is comprised of two or more capacitors in parallel, and means for connecting the reactance to, and disconnecting the reactance from, the single loop or coil, the means enabling each of the capacitors to be individually connected to, and disconnected from, the single loop or coil.

26. The frequency detection system of claim 25 wherein the means for connecting the reactance to, and disconnecting the reactance from, the single loop or coil comprises one mechanical or electrical switch for each of the capacitors.

27. A frequency detection system comprising:

a high temperature superconductor self-resonant transmit coil;

a circuit to adjust the resonance frequency of the high temperature superconductor self-resonant transmit coil, wherein the circuit comprises a single loop or coil to inductively couple the circuit to the high temperature superconductor self-resonant transmit coil;

a variable reactance in series with the single loop or coil, wherein the reactance is comprised of two or more inductors in series, and means for connecting the reactance to, and disconnecting the reactance from, the single loop or coil, the means enabling each of the two or more inductors to be individually connected to, and disconnected from, the single loop or coil.

28. The frequency detection system of claim 27 wherein the means for connecting the reactance to, and disconnecting the reactance from, the single loop or coil comprises one mechanical or electrical switch for each of the inductors.

29. A frequency detection system comprising:

a high temperature superconductor self-resonant receive coil;

a circuit to adjust the resonance frequency of the high temperature superconductor self-resonant receive coil, wherein the circuit comprises a single loop or coil to inductively couple the circuit to the high temperature superconductor self-resonant transmit coil;

a variable reactance in series with the single loop or coil, wherein the reactance is comprised of two or more capacitors in parallel, and means for connecting the reactance to, and disconnecting the reactance from, the single loop or coil, the means enabling each of the capacitors to be individually connected to, and disconnected from, the single loop or coil.

30. The frequency detection system of claim 29 wherein the means for connecting the reactance to, and disconnecting the reactance from, the single loop or coil comprises one mechanical or electrical switch for each of the capacitor.

31. A frequency detection system comprising:

a high temperature superconductor self-resonant receive coil;

a circuit to adjust the resonance frequency of the high temperature superconductor self-resonant receive coil, wherein the circuit comprises a single loop or coil to inductively couple the circuit to the high temperature superconductor self-resonant transmit coil;

a variable reactance in series with the single loop or coil, wherein the reactance is comprised of two or more inductors in series, and means for connecting the reactance to, and disconnecting the reactance from, the single loop or coil, the means enabling each of the inductors to be individually connected to, and disconnected from, the single loop or coil.

32. The frequency detection system of claim 31 wherein the means for connecting the reactance to, and disconnecting the reactance from, the single loop or coil comprises one mechanical or electrical switch for each of the inductors.

33. The frequency detection system of any of claims 29-31 which comprises a nuclear quadrupole resonance detection system.

34. The frequency detection system of claim 33 wherein the nuclear quadrupole resonance detection system detects explosives, drugs or other contraband.

* * * * *